United States Patent
Bulan et al.

(10) Patent No.: US 12,275,689 B2
(45) Date of Patent: Apr. 15, 2025

(54) METHOD FOR THE RECYCLING OF POLYURETHANE MATERIAL WASTE FOR PRODUCING CHEMICAL FEEDSTOCK FOR THE PRODUCTION OF ISOCYANATES AND POLYURETHANES

(71) Applicant: COVESTRO INTELLECTUAL PROPERTY GMBH & CO. KG, Leverkusen (DE)

(72) Inventors: Andreas Bulan, Langenfeld (DE); Rainer Weber, Odenthal (DE)

(73) Assignee: COVESTRO INTELLECTUAL PROPERTY GMBH & CO. KG, Leverkusen (DE)

( * ) Notice: Subject to any disclaimer, the term of this patent is extended or adjusted under 35 U.S.C. 154(b) by 644 days.

(21) Appl. No.: 17/614,626

(22) PCT Filed: May 26, 2020

(86) PCT No.: PCT/EP2020/064486
§ 371 (c)(1),
(2) Date: Nov. 29, 2021

(87) PCT Pub. No.: WO2020/239716
PCT Pub. Date: Dec. 3, 2020

(65) Prior Publication Data
US 2022/0227701 A1     Jul. 21, 2022

(30) Foreign Application Priority Data
May 27, 2019 (EP) .................................... 19176668

(51) Int. Cl.
*C08G 18/00*     (2006.01)
*C07C 263/10*     (2006.01)
*C08J 11/10*     (2006.01)
*C10B 53/07*     (2006.01)
*C25B 1/00*     (2021.01)

(52) U.S. Cl.
CPC ............ *C07C 263/10* (2013.01); *C08G 18/00* (2013.01); *C08J 11/10* (2013.01); *C10B 53/07* (2013.01); *C25B 1/00* (2013.01)

(58) Field of Classification Search
USPC .......................................................... 521/49
See application file for complete search history.

(56) References Cited

U.S. PATENT DOCUMENTS

| 4,243,560 | A | * | 1/1981 | Balestrini | ............... C10B 53/00 521/49 |
|---|---|---|---|---|---|
| 2007/0276154 | A1 | | 11/2007 | Haas et al. | |
| 2018/0194632 | A1 | * | 7/2018 | Jakobsson | ................. C25B 1/00 |

FOREIGN PATENT DOCUMENTS

EP     3626861 A1     3/2020

OTHER PUBLICATIONS

International Search Report and Written Opinion received for PCT Patent Application No. PCT/EP2020/064486, mailed on Sep. 9, 2020, 17 pages (8 pages of English Translation and 9 pages of Original Document).

* cited by examiner

*Primary Examiner* — Terressa Boykin
(74) *Attorney, Agent, or Firm* — K&L Gates LLP

(57) ABSTRACT

The invention relates to a method for recycling polyurethane material waste (18*a*) for producing chemical feedstock for the production of isocyanates (10*a*) and then polyurethanes (16*a*), in which method, proceeding from polyurethane material waste (18*a*), carbon dioxide (1*a*) and hydrocarbons (1*c*) are generated by pyrolysis (1), the carbon dioxide (1*a*; 4*a*) is converted by electrolysis (5) into carbon monoxide (7*b*) and hydrogen (7*a*), as appropriate, the carbon monoxide (7*b*; 7*c*) obtained is converted via phosgene to isocyanate (10*a*) and the isocyanate (10*a*) can be further processed into new polyurethane material (16*a*).

16 Claims, 1 Drawing Sheet

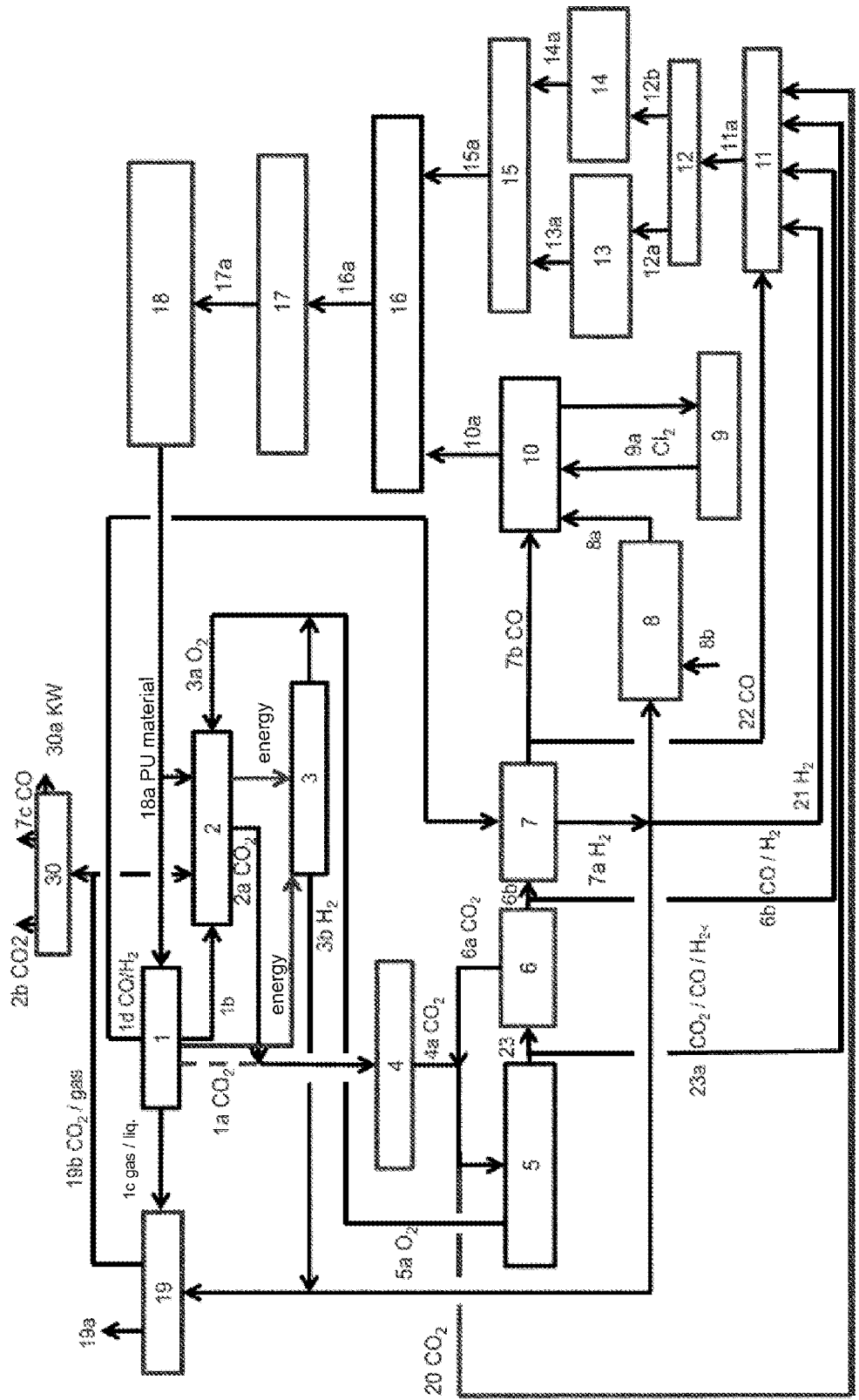

METHOD FOR THE RECYCLING OF POLYURETHANE MATERIAL WASTE FOR PRODUCING CHEMICAL FEEDSTOCK FOR THE PRODUCTION OF ISOCYANATES AND POLYURETHANES

CROSS-REFERENCE TO RELATED APPLICATIONS

This application is a national stage application (under 35 U.S.C. § 371) of PCT/EP2020/064486, filed May 26, 2020, which claims benefit of European Application No. 19176668.2, filed May 27, 2019, both of which are incorporated herein by reference in their entirety.

The invention relates to a method for recycling polyurethane material waste for producing chemical feedstock for the production of isocyanates and then polyurethanes, in which method, starting from polyurethane material waste, carbon dioxide and hydrocarbons and possibly carbon monoxide and hydrogen are generated by pyrolysis, the carbon dioxide is converted by electrolysis to carbon monoxide and possibly hydrogen, the carbon monoxide obtained is converted via phosgene to isocyanate and the isocyanate can be further processed into new polyurethane material.

The invention relates in particular to a method for the low-emission production of isocyanates and polyols using the electrochemical conversion of carbon dioxide to carbon monoxide and possibly hydrogen and the production of oxygen and the use of oxygen for incinerating materials containing polyurethane to obtain carbon dioxide and optionally incinerating pyrolysis residues obtained from materials containing polyurethane and use of the carbon dioxide respectively obtained as a raw material for the electrochemical $CO_2$ reduction. The carbon monoxide produced is used for the production of isocyanates and optionally for the production of methanol as a precursor for polyalkylene oxides.

The carbon monoxide obtained and any $CO_2$ produced is then optionally further converted with hydrogen to methanol and this is further converted by the methanol to olefin (MTO) process or specifically the methanol to propene (MTP) process to give propene as main component. The propene is converted to propylene oxide and this is then converted to polyethers. Another part of the carbon monoxide is reacted with chlorine to form phosgene and this is reacted with amines to form isocyanates. Polyurethane materials can be produced again from the isocyanates and the polyethers. This means that a large part of the value chain is closed. When using $CO_2$ and renewable energy for electrolysis, polyurethane material can be produced in a sustainable manner.

Furthermore, by integrating water electrolysis, additional hydrogen required can be produced for the hydrogenation of nitro compounds to amines, which can be converted to isocyanates with phosgene. Both in the case of electrochemical $CO_2$ reduction and in water electrolysis, the by-product oxygen is generated in each case at the anode. This oxygen can be used for incinerating the polyurethane-containing waste materials and the pyrolysis residue, whereby a highly concentrated $CO_2$ offgas stream is obtained during incineration, making $CO_2$ recovery significantly more economical than when the waste containing polyurethane material is incinerated with air.

Polyurethanes, hereinafter also referred to as PU, are plastics that result from the polyaddition reaction of dialcohols or polyols with polyisocyanates. Diols and diisocyanates result in linear polyurethanes; crosslinked polyurethanes can be produced by reacting triisocyanate-diisocyanate mixtures with triol-diol mixtures. The properties of PU can be varied within a wide range. Depending on the degree of crosslinking and/or the isocyanate or OH component used, thermosets, thermoplastics or elastomers are obtained. However, polyurethanes are also used as molding compositions for compression molding, as casting resins (isocyanate resins), as (textile) elastic fibers, polyurethane varnishes and as polyurethane adhesives. It is also very easy to produce foams from polyurethane.

Flexible PU foams are used for a wide variety of purposes, especially as upholstery material, for example for furniture and car seats, as mattress foam, as carpet backing material, for textile lamination, as cleaning sponge or as filter material.

PU rigid foams are mainly used for thermal insulation, for example in buildings, cooling devices, hot and cold storage and some pipe systems (plastic jacket composite pipes, flexible composite pipes).

There are other, relatively new areas of application for PU foams in vehicle construction, such as steering wheels, arm rests, soft coating of handles, interior trim, dashboards, sound insulation, rattle protection, seals, transparent coating of wood decors.

At the end of the use phase of the products containing PU material, they are usually disposed of, i.e. stored in landfills or incinerated in waste incineration plants. It has not yet been possible to date to carry out material use in an economically successful manner, i.e. it has not yet been possible to recover the polyols or isocyanates used from the PU materials in an economical yield.

One approach to material recycling is glycolysis, in which the urethane group is reacted with glycol to form carbamate and a polyol.

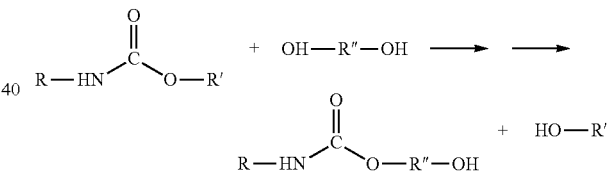

The urethane group can also be reacted with an amine to form urea and a polyol.

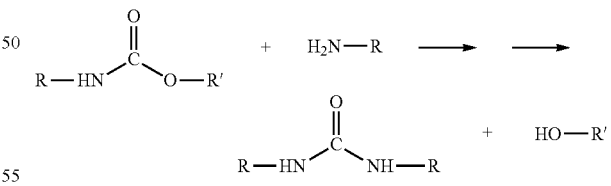

The object of the present invention was to find a sustainable alternative method for isocyanate production and ultimately also for polyurethane production, including recycling processes and closing the value chains. To date, essential components for polyurethane production, such as carbon monoxide, hydrogen and propene or ethene or oxides thereof for the production of polyols have been produced from fossil fuels. For example, carbon monoxide and hydrogen are conventionally produced from natural gas and coal by reforming processes, and propene and ethene from petroleum fractions.

One object of the invention is therefore to reduce the material use of fossil raw materials and possibly also the energetic use of fossil raw materials for isocyanate production. This is intended to further improve the carbon dioxide balance (carbon footprint) of PU production.

The invention relates to a method for recycling waste containing polyurethane material for producing chemical feedstock for the production of isocyanates and polyurethanes by a) pyrolysis of the polyurethane material at elevated temperature, optionally in the presence of a catalyst, to obtain a mixture of aliphatic and aromatic low molecular weight hydrocarbons and nitrogenous hydrocarbons, with or without carbon dioxide, with or without carbon monoxide, with or without hydrogen, and a residue of higher molecular weight hydrocarbons, b) optionally refining the mixture of low molecular weight hydrocarbons obtained in step a) to obtain a mixture of gaseous and liquid hydrocarbons and a mixture of carbon dioxide, carbon monoxide and other gaseous low molecular weight hydrocarbon compounds, and separation of the resulting mixtures and, c) incinerating the residue obtained in step a) and optionally further polyurethane material waste with oxygen-containing gas, in particular with pure oxygen, to obtain gas containing carbon dioxide, d) purifying the carbon dioxide, obtained from step c) and possibly from step a), of secondary constituents, in particular nitrogen oxides, sulfur compounds, dust, water, oxygen and HCl, optionally by means of adsorption, membrane processes or gas scrubbing, or catalytic treatment, to obtain purified carbon dioxide, e) electrolysis of the purified carbon dioxide obtained in step d), in particular electrochemical conversion of the carbon dioxide at a gas diffusion electrode, to obtain a mixture of at least carbon monoxide, unconverted carbon dioxide and possibly hydrogen, f) separating the unconverted carbon dioxide from the mixture obtained in step e) to obtain a mixture of at least carbon monoxide and possibly hydrogen and recycling the unconverted carbon dioxide to the electrolysis, g) optionally separating the hydrogen possibly obtained from the mixture of carbon monoxide and possibly hydrogen obtained in step f), h) reacting the carbon monoxide obtained from step g) or f) with chlorine to form phosgene in a process for producing isocyanate, i) optionally reacting the isocyanate obtained from step h) with polyether and optionally additionally with polyester to give a finished polyurethane material.

The oxygen for the incineration in step c) is preferably obtained from water electrolysis.

By using electricity from sustainable energy generation (wind power, hydropower, solar energy), the $CO_2$ emissions in the overall method are further reduced. In a preferred novel method, the hydrogen formed in the water electrolysis is optionally used in the optional refining and/or in a hydrogenation of nitroaromatics, wherein the amines obtained in the hydrogenation of nitroaromatics can be used in the isocyanate production. The separated hydrogen possibly obtained in step g) of the novel method is preferably used in the hydrogenation of nitroaromatics. This makes amines available as precursors of the isocyanate.

In a particularly preferred embodiment of the method according to the invention, the resource cycle is further closed in that the polyurethane material is recycled after its use to form polyurethane waste material and the isolated polyurethane waste is used as feed material in step a) of the overall method.

In the refining according to step b), further gaseous low molecular weight hydrocarbon compounds are understood to mean here in particular possibly nitrogen-containing $C_1$ to $C_4$-hydrocarbons.

When recycling PU material after the end of its useful life, conventional separation processes are used to separate composite materials in the waste. Thus, the PU material is coarsely separated automatically or manually, then mechanically shredded and, if necessary, further separated. The PU material obtained is used as a feedstock for incineration or pyrolysis.

In the case of the incineration in step c), the PU material is reacted with pure oxygen $O_2$ for example, which is evolved at the anode as by-product of the $CO_2$ electrolysis or the optional water electrolysis. The heat of reaction resulting from the incineration in step c) can be used to produce steam and/or electrical current. In particular, the heat can be used to operate the pyrolysis in step a) and the electrical current generated can be used in the electrolysis in step e). This further improves the efficiency of the novel overall method.

The $CO_2$ originating from the incineration in step c) is obtained in highly concentrated form and is fed to a purification in step d) before further use. In this process, the by-products of the incineration, for example sulfur compounds such as $SO_2$, nitrogen compounds such as NOx and residual organics as well as dust and other compounds formed from the components present in the PU material, are separated.

The incineration of the PU material with pure oxygen according to step c) can be carried out, for example, according to the process known as the oxy-fuel process in an atmosphere of pure oxygen and $CO_2$ (recirculating flue gas). The resulting flue gas is not diluted with the nitrogen present in air and consists essentially of $CO_2$ and water vapor. The water vapor can be easily condensed, so that a highly concentrated $CO_2$ stream (concentration in the ideal case close to 100 percent) is formed. The $CO_2$ can then be purified and further processed, optionally also compressed and stored.

Furthermore, some of the energy obtained from the pyrolysis in step a) or the incineration in step c) of the polyurethane material can be converted into steam or electricity. The electricity obtained can be used to operate the electrolysis in step e), resulting in an even more efficient process with low consumption of electrical energy.

The purification of $CO_2$ from combustion gases can be carried out using methods known in principle from the prior art. This is described in the following by way of example.

First, for example, the combustion gases are purified, the main component of which is $CO_2$. The assembly of a combustion gas purification system is divided into different stages. The particular task of the purification is to provide $CO_2$ without secondary constituents that disrupt the subsequent preferred electrochemical reduction of $CO_2$ at a gas diffusion electrode, described below.

In the first stage, dust is removed from the combustion gas. This can be done with fabric filters or with an electrostatic filter. Any acidic gas present, such as hydrogen chloride, which is formed from chlorine compounds present in the waste, can then be removed. Offgas scrubbing towers are used here, for example. The combustion gas is also cooled here and freed from further dusts and possibly heavy metals. In addition, sulfur dioxide gas formed is also separated off in a scrubbing circuit and converted into gypsum, for example with hydrated lime. The removal of nitrogen compounds from the combustion gases can be carried out, for example, on catalyst-containing zeolites or by adding urea or ammonia, to convert the nitrogen oxides back to nitrogen and water. In order to prevent the formation of ammonium salts, which would clog the pores of the catalyst, the catalysts are usually operated at a temperature of above 320° C. (described in principle by way of example at: https://de.wikipedia.org/wiki/Rauchgasreinigung). Likewise, the $N_2$ compounds can be removed by scrubbing with nitric acid or with catalysts.

The $CO_2$ can be dried and further purified by known conventional methods. Drying, for example, by treatment with conc. sulfuric acid.

In the final purification stage, activated carbon filters are used to remove residual organics and any last metal residues from the combustion gas using activated carbon. For this purpose, for example, activated carbon in the form of dust can be metered into the combustion gas stream or flue gas stream and then deposited again on the fabric filter together with the accumulated pollutants. The spent carbon is discharged and fed to energy recovery (described in principle in: https://www.ava-augsburg.de/umwelt/rauchgasreinigung/).

After the purification processes of the combustion gases have been carried out, $CO_2$ is available, which can be used as feedstock in step e).

Optionally, $CO_2$ can also be removed by means of amine scrubbing from gas streams with a lower concentration of $CO_2$.

The PU material recycled and comminuted as described above can be fed to the pyrolysis in step a), it being possible for the pyrolysis to be carried out either with or without a catalyst.

The fractions produced during pyrolysis are gaseous, liquid and solid, with the solid phase mostly consisting mainly of pyrolytic carbon. The liquid long-chain carbon compounds containing aromatics such as toluene, benzene, xylene are preferably fed to a refining process in step c). Here, the compounds can be separated or further reacted in refining processes with hydrogen, preferably hydrogen from water electrolysis, as appropriate, so that propene and ethene (as precursors for polyols, polyethers) can also be obtained as a result. The long-chain, liquid hydrocarbon compounds can be separated and processed further. The aromatic compounds such as benzene or aniline or, if they occur, isocyanates, could also be reused as feedstock in the appropriate syntheses.

Furthermore, the pyrolysis in step a) can optionally be operated in particular in such a way that larger amounts of carbon monoxide and possibly hydrogen are generated. These gases can be separated off together with the short-chain hydrocarbon compounds, for example in the refining step, or they can also be separated off separately and then fed to a carbon monoxide-hydrogen separation (7) and be used.

The solid substances obtained during the pyrolysis in step a) mostly consist of carbon. This solid phase can be reacted with pure oxygen from the $CO_2$ electrolysis or from the preferred water electrolysis used. This also forms a highly concentrated stream of $CO_2$, which is fed to a purification step.

Another possibility to produce high-purity $CO_2$ is to absorb the $CO_2$ in alkaline solution, for example aqueous potassium hydroxide solution. Here, potassium hydrogen carbonate is formed, which can then be thermally decomposed back to $CO_2$ and potassium hydroxide. Heat generated from pyrolysis or incineration can be used here.

The purified $CO_2$ is preferably fed to the cathode space of a $CO_2$ electrolysis according to step e).

Here, the $CO_2$ electrolysis may be, for example, a high-temperature electrolysis, which is operated at a temperature of more than 600° C., possibly with the addition of water for the production of synthesis gas. High-temperature electrolyses are known in principle and available on the market, e.g. from Haldor Topsoe, eCOs™ (https://www.topsoe.com/processes/carbon-monoxide/site-carbon-monoxide). During high-temperature electrolysis, oxygen is also produced at the anode. The disadvantage of the known high-temperature electrolysis is its poor scale-up capability, so that for larger amounts of CO, for example more than 1 t/h CO, low-temperature electrolysis is currently still preferable.

If the $CO_2$ electrolysis is operated as a low-temperature electrolysis, the electrolysis takes place at a temperature below 150° C.

With all $CO_2$ electrolyses, the purified $CO_2$ gas is fed to the cathode space.

In the case of low-temperature electrolysis, $CO_2$ is in particular converted to carbon monoxide and possibly hydrogen at a gas diffusion electrode. At the same time, $O_2$ or possibly alternatively also chlorine can be generated at the anode.

According to known principles, an MEA (membrane electrode assembly) concept can also be used in low-temperature electrolysis. In this case, a catalyst is applied to the membrane. A gas diffusion layer in front of it regulates the gas and liquid transport. This can be effected on both the anode and the cathode side. It is also possible to bring a gas diffusion electrode into direct contact with the membrane.

If chlorine is generated at the anode, this chlorine can be fed to the phosgene synthesis and thus to the isocyanate production as a further feedstock.

A gas diffusion electrode, for example, is installed in the cathode space. As with chlorine/alkali electrolysis, this can be carried out in a zero-gap as well as in a finite-gap arrangement (COV patent application COV 101 186).

The cathode space in which the gas diffusion electrode is operated can be fed an excess of $CO_2$. Excess means introducing more $CO_2$ than would be necessary for the stoichiometric conversion due to the flowing electric current. A gas mixture consisting of unreacted $CO_2$, CO and $H_2$ thus escapes the cathode space. The entire gas mixture can, for example, be fed directly to a methanol synthesis (stream 23). Here, the conversion of $CO_2$ to methanol with, if necessary, additionally fed hydrogen and the conversion of CO to methanol with $H_2$ are carried out. In this case, the additionally required hydrogen is optionally obtained from a water electrolysis described above. In a preferred embodiment of the novel method, the mixture (6b) of carbon monoxide and possibly hydrogen obtained in step f) is fed to a methanol synthesis (11). The methanol 11a is then also a precursor of the polyether production.

If carbon monoxide is to be separated from the gas mixture taken from the cathode space during $CO_2$ electrolysis, the excess unconverted $CO_2$ is first removed in step f) by a gas separation (6), for example by an amine scrubber, and the residual gas consisting of CO and $H_2$ is fed to a gas separation unit (7) in step g). The CO obtained in step g) is then fed to the isocyanate production (10), in which it is reacted with chlorine, for example from an HCl recycling process (9), to form phosgene and the phosgene is reacted with amines (8a) (particularly with diamines) to form isocyanate (in particular to form diisocyanates) in the isocyanate production (10).

The hydrogen obtained from the water electrolysis 3 or the gas separation (7) in step g) can either be fed to the hydrogenation of the nitroaromatics to amines (8a) and thus to the production of the isocyanates (10) or to the methanol production (11).

One embodiment of the novel method is therefore preferred in which at least partial streams of the carbon monoxide (22) and/or of the hydrogen (21) from the gas separation (7) are fed to a methanol synthesis (11).

In a further preferred embodiment of the novel method, the methanol 11a formed in the methanol synthesis preferably used is fed to a methanol to olefin (MTO) process (12) and the alkenes obtained therefrom are then fed to a process (13) or (14) for producing alkylene oxides, especially propylene oxide (13 a) and/or ethylene oxide (14 a).

In a particularly preferred embodiment of the novel method, following this preferred production of alkylene oxides, the propylene oxide (13 a) and/or the ethylene oxide (14 a) from the propylene oxide production (13) or from the ethylene oxide production (14) is fed to a polyether production (15) and the polyether (15 a) obtained therefrom is used in the production process (16) for producing new polyurethane material.

This also makes the other raw material required for polyurethane production, the polyether, accessible in a particularly resource-saving manner.

In a preferred variant of the novel method, the gas mixture (19 b) of carbon dioxide, carbon monoxide and gaseous hydrocarbons possibly obtained in the refining in step b) is also fed to the incineration (2) in step c).

Alternatively, in a preferred further variant of the novel method, the gas mixture (19 b) of carbon dioxide, carbon monoxide and gaseous hydrocarbons possibly obtained in the refining in step b) is separated in a gas separation (30) into the components: carbon dioxide (2b), carbon monoxide (7c) and hydrocarbons (30a) and the separated components (2b; 7c; 30a) are reused individually; in particular, the separated carbon dioxide (2b) is fed to the purification (4) in step d).

In a particularly preferred embodiment, the carbon monoxide (7c) obtained from the aforementioned optional gas separation 30 is fed to the isocyanate production (10), for example to amine production as described above.

The novel method can also preferably be operated in such a way that part of the polyurethane material is fed directly to the incineration (2) in step c) instead of the pyrolysis 1 in step a).

One embodiment of the novel method is also preferred in which at least part of the mixture (23) of carbon dioxide, carbon monoxide and possibly hydrogen obtained in step e) from the electrolysis (5) is fed directly to the methanol synthesis (11) described above.

In a preferred variant of the novel method, oxygen, which is formed in the reaction by electrolysis (5) of carbon dioxide (4a) in step e), is at least partially fed to the incineration (2) in step c).

In one preferred novel method, the overall material balance is further improved by feeding part of the carbon dioxide (6a) obtained in the separation (6) in step f) optionally into the input stream (4a) of the electrolysis (5) in step e) and/or to the optional methanol synthesis (11).

The hydrogen chloride (HCl) produced during the production of isocyanates may be fed to the low-temperature $CO_2$ electrolysis (5) (not shown in FIG. 1) or another HCl recycling unit (9) such as an HCl diaphragm or HCl electrolysis with gas diffusion electrode or a catalytic gas phase oxidation. In the case of HCl electrolysis with a gas diffusion electrode or gas phase oxidation, the $O_2$ required can be obtained from the low-temperature or high-temperature $CO_2$ electrolysis (5) and/or water electrolysis (3) (not shown in FIG. 1).

The methanol produced in the preferred embodiments of the novel method is converted to propene or ethene, for example, by the MTO (methanol to olefin) process (12), which is known in principle. The by-products formed in this case can be fed to the optional refining (19) in step b) and thus become accessible for further useful recycling. From the propene and ethene of the MTO process (12), propylene oxide (13a) and ethylene oxide (14a) can be produced via the known processes, from which, for example, the polyethers (15a) can be produced. With the isocyanates and the polyethers and, optionally, additionally with polyesters, the PU materials (16a) required on the market can then be produced. The polyurethanes are used in various applications (17). At the end of their useful life, the materials are fed to recycling (18) and the PU materials are separated here. The separated material is then fed again to pyrolysis (1) and/or incineration (2).

This means that no further fossil raw materials are required for isocyanate production and polyurethane material can be produced in a sustainable manner.

The invention is illustrated in detail by way of example hereinafter with reference to the FIGURES.

In the FIGURES below:

FIG. 1 shows a schematic overview of the overall method including PU production, use and recycling In FIG. 1, the following reference numbers have the meaning on the right in each case:

1 pyrolysis unit
1a $CO_2$ from pyrolysis (optionally, the gaseous components are fed to a $CO_2$ separation (potassium hydroxide, $KHCO_3$ formation and decomposition thereof—not shown)
1b residual solid from the pyrolysis
1c gaseous and liquid components from the pyrolysis
1d CO-hydrogen mixture from the pyrolysis
2 incineration of PU material with pure oxygen
2a $CO_2$ gas stream from incineration 2
3 optional water electrolysis
3a oxygen from water electrolysis, anode space
3b hydrogen from water electrolysis, cathode space
4 $CO_2$ purification
4a $CO_2$ purified gas stream
5 $CO_2$ electrolysis
5a $O_2$ from the $CO_2$ electrolysis, anode space
6 $CO_2$ removal from CO, Hz, $CO_2$ gas mixture
6a $CO_2$ gas stream from $CO_2$ separation
6b CO/Hz separated from $CO_2$ separation
7 $CO_2$—$H_2$ gas separation
7a hydrogen from gas separation CO—H2 7
7b carbon monoxide from gas separation CO—H2 7
7c carbon monoxide from gas separation 30
8 hydrogenation of nitroaromatics
8a amines
8b nitroaromatics
9 HCl recycling
9a chlorine from HCl recycling
10 isocyanate production
10 a isocyanates
11 methanol synthesis
11a methanol 12 methanol to olefin process (MTO)
12a propene
12b ethene
13 propylene oxide production
13a propylene oxide
14 ethylene oxide production
14a ethylene oxide
15 polyether production
15a polyether
16 polyurethane material production
16a PU material
17 market—use of polyurethane materials until end of use
17a PU material used
18 recycling of used polyurethane material with isolation of the polyurethane component
18a polyurethane material for pyrolysis or incineration
19 refining
19a products from refining
19b $CO_2$/CO and non-separated gaseous compounds
20 $CO_2$ from $CO_2$ purification 4 or $CO_2$ removal 6 for methanol synthesis 11
21 hydrogen from CO—$H_2$ gas separation 7 or water electrolysis 3
22 CO from the CO—$H_2$ gas separation 7 (optionally from pyrolysis, not shown in FIG. 1)
23 CO, $CO_2$, $H_2$ gas mixture from the low-temperature or high-temperature $CO_2$ electrolysis
30 gas separation for $CO_2$, CO, hydrocarbons from refining 19
30a hydrocarbons from gas separation 30

EXAMPLE

Example 1 Pyrolysis with Catalyst, Incineration of the Gaseous Fraction According to FIG. 1

A PU material having an elemental composition of 66.5% by weight carbon, 6.6% by weight hydrogen, 7.2% by weight nitrogen and 18.8% by weight oxygen was used and treated in a catalytic pyrolysis 1. The PU material was previously cut into small pieces in a cutting mill, then the material was hot-pressed and shredded again so that all the particles had a diameter of less than 4 mm. This material 18a was mixed with a zeolite-based catalyst HZSM-5 in a ratio by weight of 1:1 and fed to a fluidized bed. The fluidized bed already contained pre-filled catalyst HZSM-5. The fluidized bed was operated at 600° C.

From pyrolysis 1, 25.0% by weight of the material fed in was obtained as solid residue 1b (predominantly carbon). Furthermore, 37% of the mass used was removed as gaseous products and 35% as liquid materials 1c. The gaseous compounds consisting of $CO_2$, CO, methane, ethene, ethane, propene, propane were fed directly to incineration 2 with pure oxygen without refining 19.

2838 t/a PU material from the recycling of PU insulation material from refrigerators are used. 1516 t/a are fed to pyrolysis 1 and 1322 t/a to incineration 2. From pyrolysis 1 and incineration 2, 5580 t/a $CO_2$ 1a; 2a are fed to electrolysis 5 after purification 4 of the $CO_2$. A gas mixture 23 of 3505 t/a CO and 135 t/a $H_2$ can be extracted from electrolysis 5. Furthermore, 3081 t/a $O_2$ 5a are removed from the anode space of the electrolysis and fed to the incineration 2 of the PU material 18a or the residue 1b.

The electrolysis 5 is expediently operated in accordance with the European patent application number 18195279.7, example 1. 160 elements of 2.5 m² electrode area each ($CO_2$ GDE) are required, which are connected together to form an electrolyser. The operating time is 8500 hours per year. The electrolysis is operated at a cell voltage of 3.17 V with a current yield with respect to CO of 68%. 32 722 MWh of renewable energy, especially with wind power, are used.

The gaseous compounds 19b from pyrolysis 1 are fed to incineration 2. The solid compounds 1b from pyrolysis 1 are also fed to an incineration 2.

From the liquid fraction of pyrolysis 1, 182 t/a heterocycles, 139 t/a benzene/toluene mixture, 27 t/a xylene and naphthalene mixture and 182 t/a aniline can be obtained with an additional refining 19.

The gas mixture 23 produced from the low-temperature electrolysis 5 is fed to an amine scrubber and the unreacted $CO_2$ is separated from the mixture 23 and returned to the electrolysis 5. The gas 6b freed of $CO_2$ consisting of CO and $H_2$ is fed to a CO—$H_2$ separation in the form of a cold box 7 in which CO and $H_2$ are separated. The CO 7b is reacted with the $Cl_2$ 9a originating from the HCl recycling 9 to form phosgene and this is reacted with aniline to form isocyanate 10a.

A partial stream of the gas mixture 23a from the electrolysis 5 consisting of $CO_2$, CO and $H_2$ is fed to the methanol synthesis after drying and the hydrogen 3b required for the reaction is also obtained from the water electrolysis 3. The methanol 11a is then converted to propylene 12a and the by-product ethylene 12b by means of the MTO process, which are further converted into propylene oxide 13a and ethylene oxide 14a in stages 13 and 14 respectively. Any missing amounts of propylene/ethylene are supplied from other manufacturing processes. In the polyether production 15, the polyols 15a required for the PU material production are produced from the alkyl oxides. New PU material 16a is produced from the isocyanates 10a and the polyols 14a. After use as used PU material 17a, this can be fed to recycling 18 for the production of PU raw material 18a for incineration 1/pyrolysis 2, thus closing the value-added cycle.

The invention claimed is:

1. A method for recycling waste containing polyurethane material for producing chemical feedstock for the production of isocyanates and polyurethanes by
   a) pyrolysis of the polyurethane material at elevated temperature, optionally in the presence of a catalyst, to obtain a mixture of aliphatic and aromatic low molecular weight hydrocarbons and nitrogenous hydrocarbons, with or without carbon dioxide, with or without carbon monoxide, with or without hydrogen, and a residue of higher molecular weight carbon compounds,
   b) optionally refining the mixture of low molecular weight hydrocarbons obtained in step a) to obtain a mixture of gaseous and liquid hydrocarbons and a mixture of carbon dioxide and carbon monoxide, hydrogen and other gaseous hydrocarbon compounds, and separation of the resulting mixtures in a gas separation;
   c) incinerating said residue obtained in step a) and optionally further polyurethane material waste with oxygen-containing gas, in particular with pure oxygen, to obtain gas containing carbon dioxide,
   d) purifying the carbon dioxide, obtained from step c) and optionally from step a), of secondary constituents, in particular nitrogen oxides, sulfur compounds, dust, water, oxygen and HCl, optionally by means of adsorption, gas scrubbing or catalytic treatment to obtain purified carbon dioxide,
   e) electrolysis of the purified carbon dioxide obtained in step d), in particular electrochemical conversion of the carbon dioxide at a gas diffusion electrode, to obtain a mixture of at least carbon monoxide, unconverted carbon dioxide and optionally hydrogen, f) separating the unconverted carbon dioxide from the mixture obtained in step e) to obtain a mixture of at least carbon monoxide and optionally hydrogen and recycling the unconverted carbon dioxide to the electrolysis, g) optionally separating the hydrogen optionally obtained from the mixture of carbon monoxide and hydrogen obtained in step f), h) reacting the carbon monoxide obtained from step g) or f) with chlorine to form phosgene in a process for producing isocyanate, i) optionally reacting the isocyanate obtained from step h) with polyethers and optionally additionally with polyester to give a finished polyurethane material.

2. The method as claimed in claim 1, wherein the oxygen for the incineration in step c) is obtained from water electrolysis or the $CO_2$ electrolysis.

3. The method as claimed in claim 2, wherein the hydrogen formed in the water electrolysis is optionally used in the refining and/or in a hydrogenation of nitroaromatics, wherein the amines obtained in the hydrogenation of nitroaromatics are used in the isocyanate production.

4. The method as claimed in claim 1, wherein the mixtures obtained in steps e) and f) comprised hydrogen, which was separated to obtain separated hydrogen in step g) is used in the hydrogenation of nitroaromatics.

5. The method as claimed in claim 1, wherein the polyurethane material is recycled after its use to form polyurethane waste material and the isolated polyurethane waste is used as feed material in step a).

6. The method as claimed in claim 1, wherein the mixture of at least carbon monoxide, optionally carbon dioxide and optionally hydrogen obtained in step e) and f) is fed to a methanol synthesis.

7. The method as claimed in claim 1, wherein at least partial streams of the carbon monoxide and/or of the hydrogen from the gas separation or the water electrolysis are fed to a methanol synthesis.

8. The method as claimed in claim 6, wherein the methanol from the methanol synthesis is fed to a methanol to olefin process and the alkenes obtained therefrom are then fed to a process for producing alkylene oxides.

9. The method as claimed in claim 8, wherein the propylene oxide and/or the ethylene oxide from the propylene oxide production or from the ethylene oxide production are fed to a polyether production and the polyether obtained therefrom is used in the production process for producing new polyurethane material.

10. The method as claimed in claim 1, wherein the refining of step b) is carried out and the gas mixture of carbon dioxide, carbon monoxide and gaseous hydrocarbons and hydrogen obtained in the refining in step b) is fed to the incineration in step c).

11. The method as claimed in claim 1, wherein the gas mixture obtained in the refining in step b) is separated in a gas separation into the components: carbon dioxide, carbon monoxide and hydrocarbons and the components are reused individually, in particular in that the carbon dioxide is fed to the purification in step d).

12. The method as claimed in claim 11, wherein the carbon monoxide from the gas separation is fed to the isocyanate production.

13. The method as claimed in claim 1, wherein additionally part of the polyurethane material is fed directly to the incineration in step c).

14. The method as claimed in claim 1, wherein at least part of the mixture of unconverted carbon dioxide, carbon monoxide and optionally hydrogen obtained in step e) from the electrolysis is fed directly to the methanol synthesis.

15. The method as claimed in claim 1, wherein oxygen is formed during the electrolysis of carbon dioxide in step e), which is at least partially fed to the incineration in step c).

16. The method as claimed in claim 1, wherein part of the carbon dioxide obtained in the separation in step f) is optionally fed into the input stream of the electrolysis in step e) and/or to the optional methanol synthesis.

* * * * *